(12) United States Patent
Bär

(10) Patent No.: US 6,635,236 B2
(45) Date of Patent: Oct. 21, 2003

(54) METHOD FOR TREATING PODOTROCHLOSIS

(76) Inventor: Knut Bär, Am Brentenberg 18, 91245 Simmelsdorf (DE)

(*) Notice: Subject to any disclaimer, the term of this patent is extended or adjusted under 35 U.S.C. 154(b) by 0 days.

(21) Appl. No.: 09/927,893

(22) Filed: Aug. 10, 2001

(65) Prior Publication Data

US 2003/0031731 A1 Feb. 13, 2003

(51) Int. Cl.⁷ .................................................. A61K 49/00
(52) U.S. Cl. .................. 424/9.1; 424/485; 424/486; 424/680; 424/484; 514/762; 514/816; 514/818; 600/9; 600/13; 600/14; 600/437; 600/439; 600/442; 601/15; 604/20; 607/2; 607/3; 607/144
(58) Field of Search .................. 604/20; 424/484, 424/485, 680, 486, 9.1; 514/762, 816, 818; 600/437, 439, 442–444, 9, 13, 14; 601/15; 607/2, 3, 144

(56) References Cited

FOREIGN PATENT DOCUMENTS

| DE | 20005438 | * 5/2001 |
|----|----------|----------|
| NL | 9201422  | * 3/1994 |

OTHER PUBLICATIONS

Revenaugh Shockwave: Wave of the Future Article#3057 The Horse.com May 2001.*
Church The Horse.com Shockwave learning Article#968 May 2001.*
Medical Engineering Siemens Analgesic— Feb. 2000.*
Schnewlin et al. Schweizer Archiv. fur Tierheilkude 143(5)227–32 May 2001.*
Reef Vet. Am. Equine Pract. 17 #159–78 2001.*
Gentle Doctor–ISU's McClure Fall 2001.*
Merck Veterinary Manual pp. 543–544 1973.*

* cited by examiner

Primary Examiner—Neil S. Levy
(74) Attorney, Agent, or Firm—Heslin Rothenberg Farley & Mesiti P.C.

(57) ABSTRACT

A method for treating podotrochlosis (navicular disease/navicular syndrome) in the foot of a horse is disclosed. The method comprises identifying the specific area(s) of the horse's foot affected by navicular disease and applying at least one extracorporeal shockwave to the affected area(s). In a preferred embodiment, a sonar-emitting device is used to identify the areas within the foot affected by podotrochlosis.

11 Claims, 3 Drawing Sheets

METHOD FOR TREATING PODOTROCHLOSIS

FIELD OF THE INVENTION

This invention relates to a method for treating podotrochlosis, or navicular disease, in the foot of a horse.

BACKGROUND OF THE INVENTION

Podotrochlosis, also known as navicular disease or navicular syndrome, is a type of lameness affecting the forelimbs of horses. The condition is almost always bilateral and is most commonly seen in middle-aged performance horses, such as hunters or show horses, for example, that are confined or stall-kept, that have high physical demands placed on them, or that are required to continuously walk over hard surfaces, such as pavement or gravel. Fast-growing breeds with small feet, such as Quarter Horses or Thoroughbreds, are at a higher risk for developing the condition than are slower-growing breeds, such as draft horses, which have larger feet in comparison to their body size.

The actual cause of the condition is not clearly understood, and thus, is frequently referred to as a syndrome (a recurring group of symptoms of unknown cause), rather than a disease. Factors that contribute to the initiation of the condition include, but are not limited to, preferential breeding for body mass and small feet, poor conformation and poor or inappropriate shoeing, that can lead to a broken hoof-pastern axis, long toes and underslung heals. Each of these factors can place unusual pressure and stress on the navicular bone, causing inflammation and pain, which ultimately leads to lameness. Probst, S., "Navicular Syndrome in Horses," *University of Illinois, College of Veterinary Medicine, Continuing Education—Public Service Extension* (2001). The uncertainty with respect to a specific causal factor, makes diagnosis, and in turn, treatment, of podotrochlosis very difficult.

In the anatomy of the horse's leg, the distal sesamoid bone, commonly known as the navicular bone, is located in the lower portion of the hoof, directly behind the pedal or coffin bone, wedged between the pedal bone and the short pastern bone. The navicular bone is connected to other bones in the hoof by the impar ligaments. The deep digital flexor tendon stretches from the pedal bone, under the navicular bone, upwards to the upper portion of the back of the horse's leg.

The navicular bone serves two important functions: 1) by being wedged between the pedal bone and short pastern, it increases the size of the pedal joint, allowing the joint to absorb more stress and concussion; and 2) it maintains the angle of the deep digital flexor tendon and acts as a pulley on the tendon, which takes a significant amount of stress off the pedal bone by absorbing a majority of it. McNamee, C., "Navicular Syndrome" www.equusite.com. (1998).

Podotrochlosis may be initiated following injury to the deep digital flexor tendon, such as bruises, adhesions, torn fibers and fibrillation or fraying. When injured, the movement of the tendon may be greatly limited, which can lead to erosion of the navicular bone. In the alternative, the navicular bone itself can deteriorate, producing jagged or sharp bone edges that can tear or otherwise injure the deep digital flexor tendon as it continually stretches over it. Poor blood supply, caused by thrombosis or blood clots, leads to low oxygen levels in the navicular bone, resulting in pain and causing deterioration of the bone. Podotrochlosis may also be the result of foot imbalance, such as medio-lateral foot imbalance, or an abnormal foot conformation, such as a long toe/low heel conformation, sheared heels or small feet, which can lead to a broken backward hoof-pastern axis.

Podotrochlosis is thus a dynamic problem, and its effects are seen with every step the horse takes. With each stride, the horse lifts up the leg, moves it, and then lowers it to bear weight. The individual anatomical parts of the foot are loaded and unloaded, stretched and relaxed, time after time. Once the condition has been initiated, the resultant pathology will include bone changes, cartilage changes, tendon changes and ligament changes.

Currently, there is no one treatment for podotrochlosis that is effective in all cases. Common non-medical treatments include rest from demanding and repetitive work and improved foot care, including trimming and shoeing. Medical treatments include drug therapy and correction of the hoof by surgery. Riegl, R J and Hakola S E, *Illustrated Atlas of Clinical Equine Anatomy and Common Disorders of the Horse*, Equista Publications, Ohio, USA (1996).

Pharmaceutical therapy may include treatment to increase vascular circulation to the feet, as well as symptomatic treatment to reduce inflammation and relieve pain. Commonly used drugs include isoxsuprine and warfarin, non-steroidal anti-inflammatory drugs (NSAIDS) and corticosteroids, and polysulfated glycosaminoglycans. Isoxsuprine is known to dilate deep blood vessels and improve circulation; warfarin is a thrombolytic drug, which dissolves blood clots and improves circulation. NSAIDS and corticosteroids reduce pain and inflammation, and some NSAIDS are also believed to reduce blood clotting. Glycosamine compounds are given to help protect cartilage from further deterioration. A more aggressive pharmaceutical therapy involves the injection of ammonium chloride into the palmar digital nerve, thus blocking pain and allowing the horse to use its foot in a normal manner.

While pharmaceutical treatment can and often does provide relief from the condition, a pharmaceutical cure for podotrochlosis has not yet been realized, and once administration of the particular chosen drug has ceased, symptoms will reoccur. In addition, it is commonly known that drug therapy is frequently associated with one or more side effects, some of which may be adverse or even fatal.

Surgical treatments include correction of the shape and position of a damaged hoof, as well as treatment to reduce pain. Correction of the hoof is recommended if a broken backwards hoof pastern axis occurs, leading to a long toe/low heel conformation, or in cases where the heels have collapsed badly. Following corrective surgery, orthopedic horse shoes are typically applied. While this type of surgery clearly has a palliative effect, it does not cure the cause for the lameness, and can not be viewed as a curative treatment.

Other surgical treatments include palmar digital neurectomy, wherein the palmar digital nerves are severed, and desmotomy, wherein the suspensory navicular ligaments are cut to relieve pressure on the navicular bone and enable the deep digital flexor muscle to stretch. With respect to neurectomy, as this procedure prevents the horse from feeling pain in the heel area (although sensation to the toe remains), careful supervision is required to avoid injury and/or infection. In addition, the benefits of this type of surgery typically last for only about a year or so, as the severed nerves will almost always regrow. McNamee, C., "Navicular Syndrome" www.equusite.com, (1998).

Thus, while there are methods for treating podotrochlosis, there is no cure. Moreover, each of the known treatments is associated with its own set of drawbacks and side effects. The present invention overcomes these disadvantages and provides a method for the treatment of podotrochlosis that yields superior, long-lasting results with minimal side-effects and trauma for the animal patient.

SUMMARY OF THE INVENTION

The present invention provides a method for treating podotrochlosis in the foot of a horse that involves the use of a sonar-emitting/shockwave-emitting device to identify specific area(s) within the foot affected by podotrochlosis and to subsequently deliver one or more extracorporeal shockwaves directly to the identified area(s).

In accordance with the principles of the invention, the hoof of an affected animal is first softened, then cut and shaped as needed, and then an anesthetic agent is administered to the animal to relax at least the deep digital flexor muscle (musculus flexor digitalis profundus) and the associated tendon, which are then flexed or extended to a desired extent. Specific areas within the foot affected by the condition are identified, preferably by use of a sonar-emitting device. Preferably, a sonar transmission-enhancing agent is applied to the hoof, prior to application of the sonar-emitting device. Once the affected areas have been identified, a shockwave-emitting device is applied to the hoof, and at least one extracorporeal shockwave is directed at each of the affected areas.

In various embodiments of the method, the hoof is softened by soaking in an aqueous solution, preferably of about 0.9% NaCl. The extent of flexion or extension of the deep digital flexor muscle and tendon will preferably result in a prolongation of between about 20% and 100%, and preferably, between about 35% and 80% of the natural length. The preferred agent for enhancing sonar transmission is paraffin.

BRIEF DESCRIPTION OF THE DRAWINGS

Preferred embodiments of the present invention will now be more particularly described, by way of example and with reference to the accompanying drawings, wherein.

DETAILED DESCRIPTION OF THE INVENTION

Figure 1:
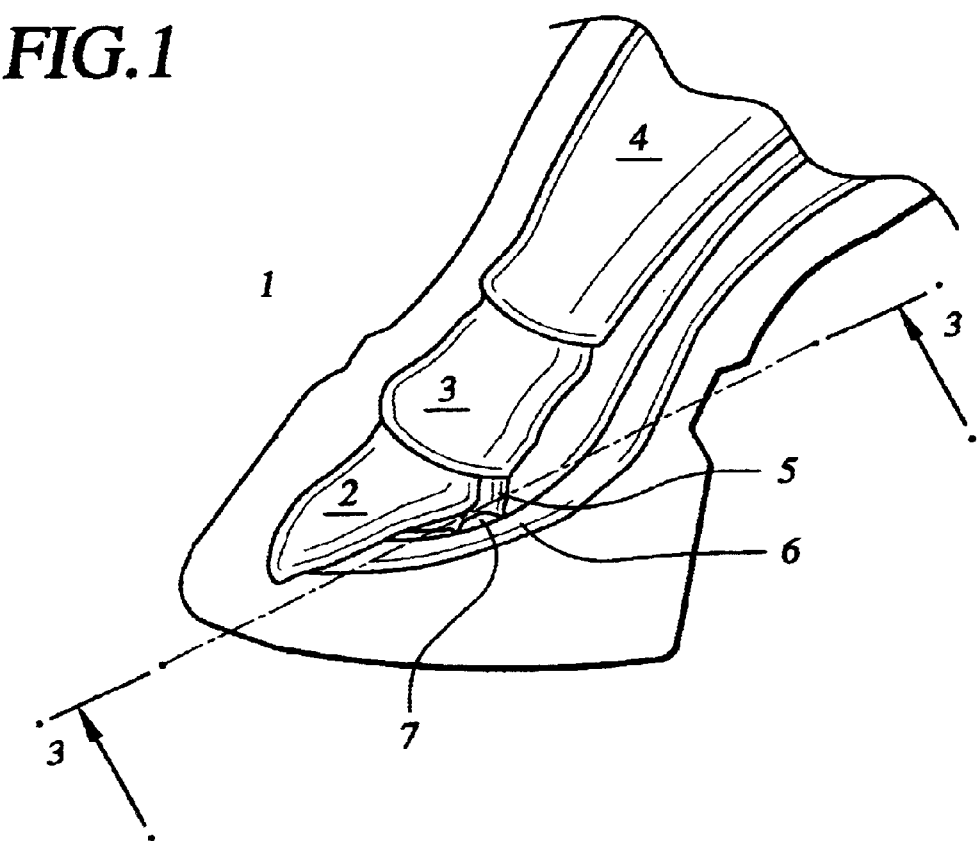
FIG. 1 is a parasagittal view of a hoof portion of a horse foot.

The method of the present invention provides an effective treatment for a confirmed medical diagnosis of podotrochlosis in the foot of a horse. The method involves the application of one or more shockwaves to the affected area(s) within the foot. The method is preferably applied to a fully anesthetized horse, although the principles of the invention also allow for application of the method wherein only the affected leg of the horse has been anesthetized. Full anesthesia of the animal is preferred as this allows the application of a higher shock pulse rate and energy, without submitting the animal to increased levels of pain.

Prior to initiating the treatment method of the present invention, it is preferable that the animal be fixed onto a typical rotatable surgery table in order to have undisturbed access to the hoof of the affected foot. The shoe is removed from the hoof, which is then softened, preferably with the application of an aqueous solution. An aqueous solution of 0.9% NaCl is a preferred softening agent. Depending upon the thickness of the hoof, this procedure may take up to an hour. The hoof is then cut, and shaped as may be needed, to provide an appropriate surface for application of the sonar-emitting/shockwave-emitting device.

Following these initial preparatory steps, an anesthetic agent is administered, in order to relax a least the deep digital flexor muscle and the associated tendon. By way of illustration, an efficient complete anesthesia of the horse may be obtained with a combination of a sedative and an anesthetic agent. Appropriate sedatives include, but are not limited to, such agents as xylazine HCl (e.g., Boehringer Ingelheim Vetmedica GmBH, Germany) 1.1 mg/kg, Domosedan™ (detomidine HCl, Orion-Farmos Corp., USA) 20 µg/kg or Sedivet® (romifidine, Boehringer Ingelheim Vetmedica GmBH, Germany) 100 µg/kg. A preferred anesthetic agent is Ketaset® (ketamine HCl, Fort Dodge Animal Health, a division of American Home Products, NY, N.Y. USA) 2.2 mg/kg. The desired sedative is administered first, followed by the anesthetic after an appropriate waiting period (with xylazine HCl, about 2 minutes; with detomidine HCl, about 5 minutes; and with romifidine, about 5–10 minutes). The anesthetic effect may be maintained during surgery with the use of an inhalable narcotic anesthetic agent such as isoflurane or halothan.

In the alternative, if circumstances do not allow for the full anesthesia of the animal, a local anesthetic may be administered, whereby only the deep digital flexor muscle and the associated tendon are affected. Effective anesthesia under these circumstances may be achieved with a combination such as detomidine HCl 12 µg/kg and Torbugesic® 4 g/kg (butorphanol tartrate, American Home Products, NY, N.Y. USA) or romifidine 60 µg/kg and Torbugesic® 20 µg/kg. The former combination should include at least a five minute waiting period between administration of the detomidine HCl and the butorphanol tartrate.

Once the anesthetic agent has taken effect, the deep digital flexor muscle and the associated tendon are stretched, either by extension or flexion, with a resulting prolongation of between about 20% and 100% of its natural length. Preferably, the prolongation is between about 35% and 80%.

Following this stretching, and prior to initiation of the treatment, due to the high density of the hoof, it is desirable, although not essential, to apply an agent to the hoof that is capable of enhancing sonar transmission through the hoof to a distal section of the foot affected by podotrochlosis. A preferred sonar transmission-enhancing agent is paraffin, although other agents may be used, so long as the agent has substantially the same shockwave transmission features as the tissue of the hoof. Such agents are commonly known and available commercially. The sonar transmission-enhancing agent is utilized to fill in the distinctive U-shaped underside of the hoof to ensure a uniform transmission of the sonar into the foot.

A sonar-emitting device is then applied to the sonar transmission-enhancing agent and sonar is emitted to detect and locate the affected area(s) within the hoof. Once the area(s) have been located, a shockwave-emitting device is utilized to direct one or more extracorporeal shockwaves into the affected area(s). Without being limited by a particular theory, it is believed that the shockwaves function to improve blood circulation within the navicular bone.

Figure 2:
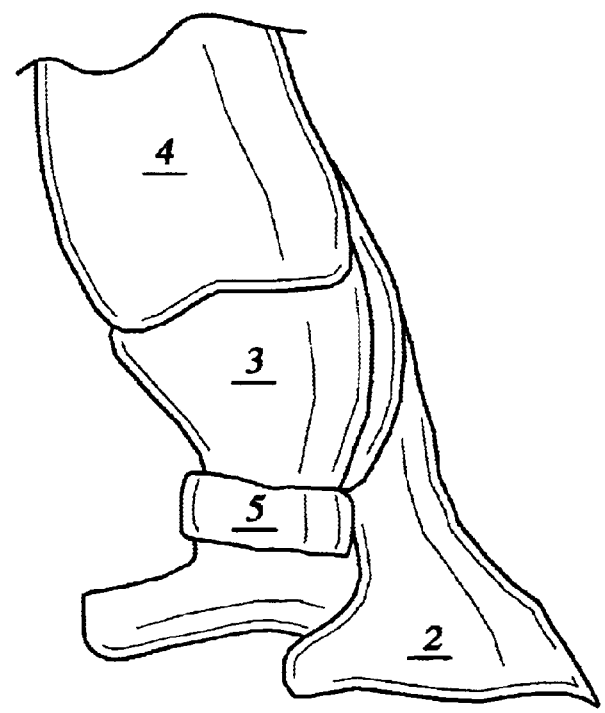
FIG. 2 is a parasagittal view of a hoof portion of a horse foot from the dorsalis perspective.

Referring specifically to the drawings, FIGS. 1 and 2 illustrate the basic anatomy of a hoof portion of a horse foot 1. FIG. 1 is a parasagittal view of hoof 1 showing the pedal or coffin bone 2, the short pastern bone 3, the long pastern bone 4 and the distal sesamoid or navicular bone 5, in addition to the deep digital flexor tendon 6, which stretches from the pedal bone 2, under the navicular bone 5 and upward to the upper rear portion of the horse's leg. Also depicted is a tendon adhesion 7, a frequently alleged cause of podotrochlosis. FIG. 2 is a parasagittal view of hoof 1, from the dorsalis perspective, showing the structural relationship of the foot bones.

Figure 3:
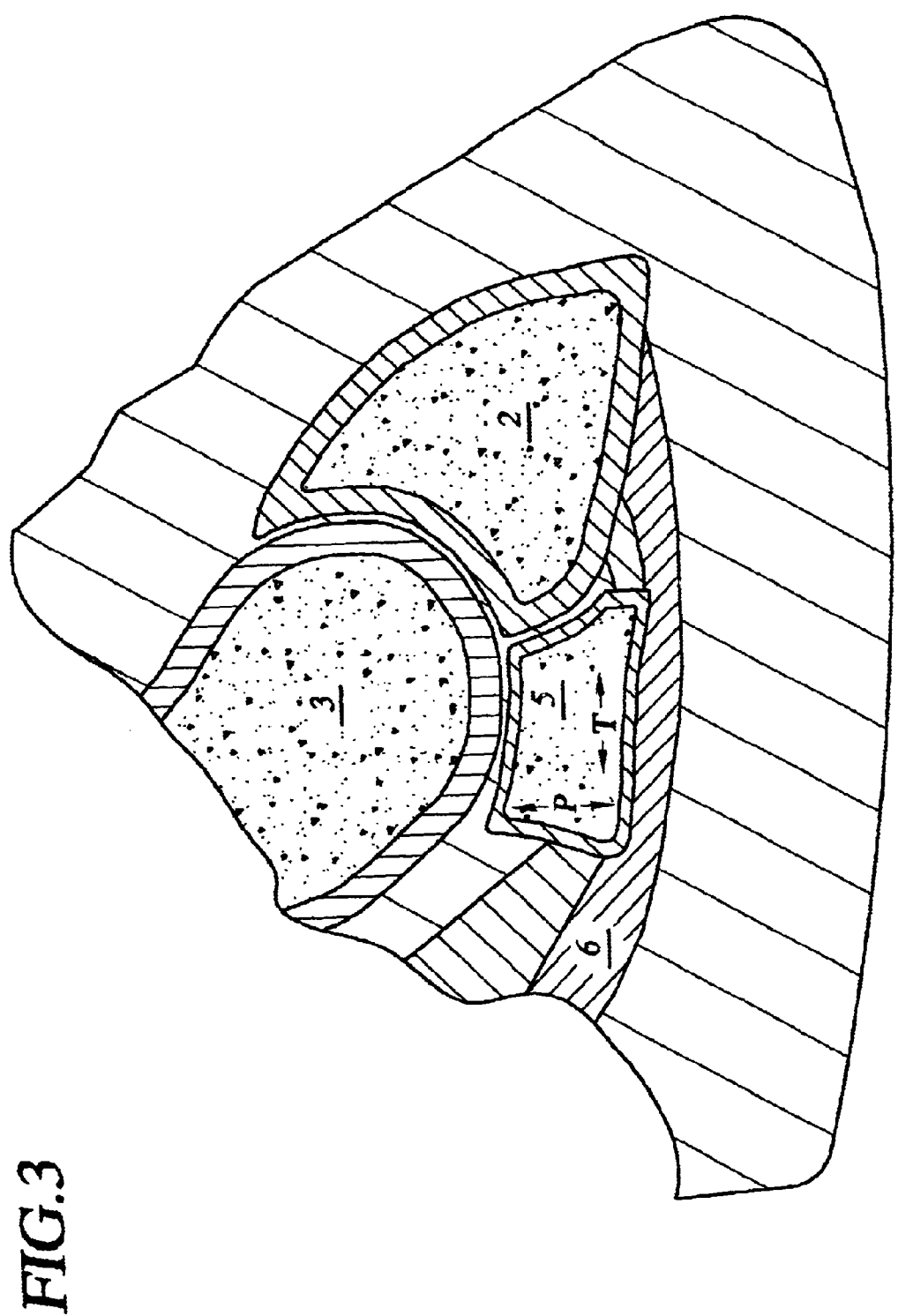
FIG. 3 is a schematic lateral view of a cross section taken along line 3—3 of FIG. 1, and extending through the short pastern bone, the pedal bone, the navicular bone and the deep digital flexor tendon.

FIG. 3 is a schematic lateral view of a cross section taken along line 3—3 of FIG. 1, again showing the relationship of the pedal bone 2, the short pastern bone 3 and the navicular bone 5, as well as the deep digital flexor tendon 6. As depicted, in FIG. 3, when weight is placed on the hoof 1, it creates pressure on tendon 6, which results in pressure ($\updownarrow P$) on both the navicular bone 5 and the short pastern bone 3. In addition, movement of the deep digital flexor tendon 6 creates tension stress ($\leftrightarrows T$) on the navicular bone 5.

Figure 4:
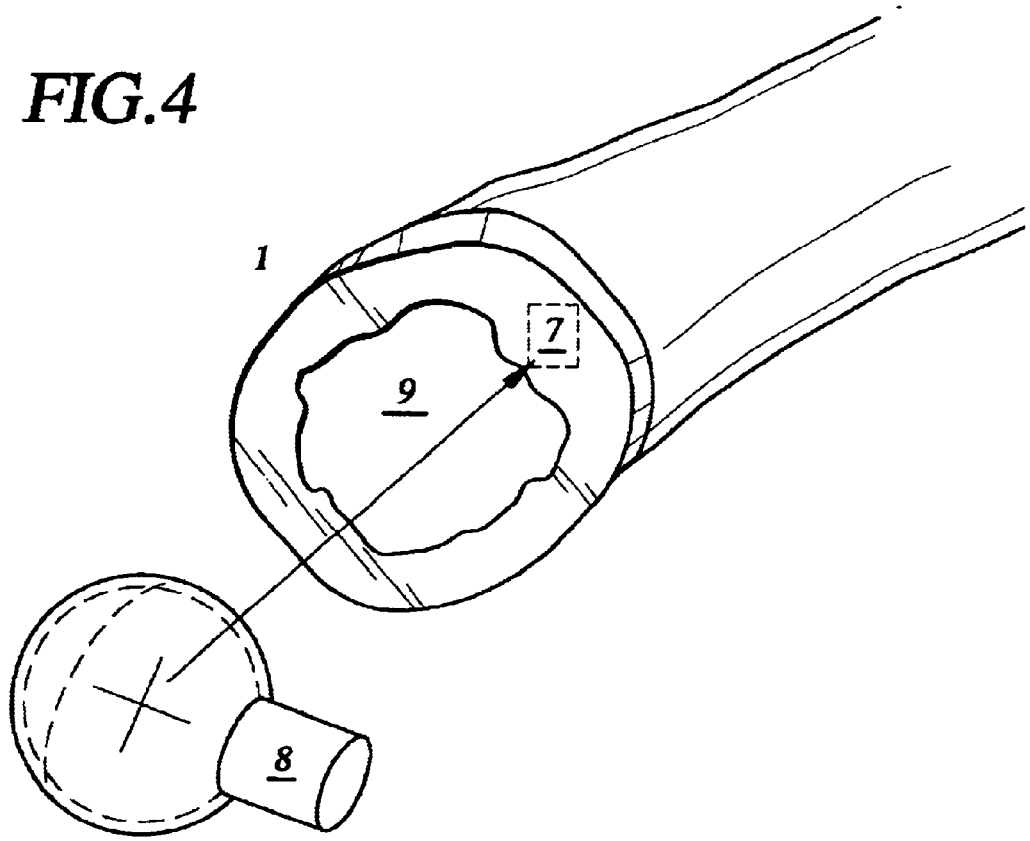
FIG. 4 is a plantaris view of a sonar-emitting/shockwave-emitting device in proximity to the underside of a hoof portion of a horse foot.

FIG. 4 depicts a typical sonar-emitting/shockwave-emitting device 8 being aligned with hoof 1, wherein the U-shaped underside is filled with sonar transmission-enhancing agent 9. In order to ensure that the shockwaves will be focused on the precise areas, such as, for example, tendon adhesion 7, within the foot affected by podotrochlosis, device 8 will preferably include features for imaging the respective sections identified by the sonar where the shockwaves are to be directed. Although a device combining all of these features greatly eases the identification of affected areas and the subsequent shockwave treatment, separate devices may be used, and are commercially available. A combination device especially well-suited for use in the method of the present invention is the SONOCUR PLUS™ (Siemens A G, Wittelsbacherplatz 2, D-80333 Munich, Federal Republic of Germany). This device includes features that allow for combined imaging and sonar-emission, as well as shockwave-emission.

Figure 5:
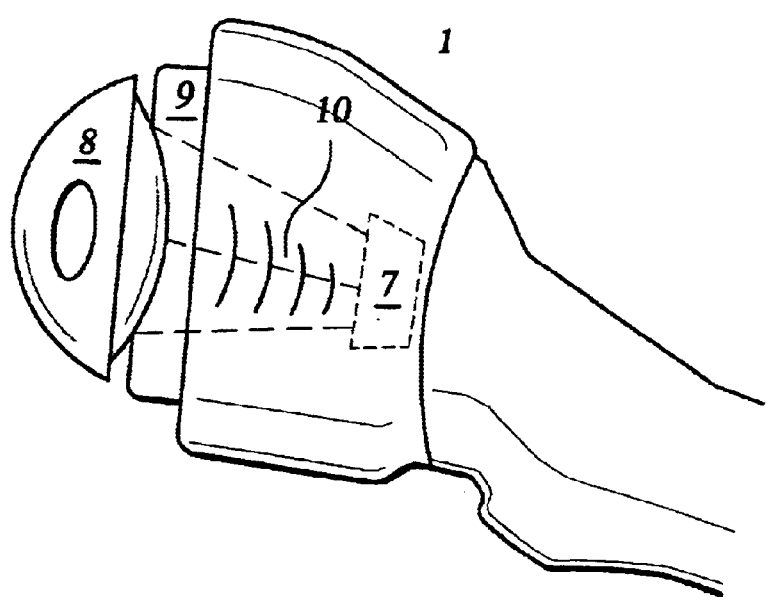
FIG. 5 shows a lateralis view of a hoof portion of a horse foot following attachment of a sonar-emitting/shockwave-emitting device.

Referring now to FIG. 5, device 8 is preferably attached to hoof 1 via a sonar transmission-enhancing agent 9. A proper attachment will ensure that there are no gaps in the point of attachment, as such air spaces can cause disturbances in transmission of the sonar and shockwaves, jointly depicted as 10. Once an affected area such as tendon adhesion 7 has been identified, device 8 directs one or more extracorporeal shockwaves into the area. The density and pulse rate of the shockwaves being emitted are determined by the state of the disease, the density of the hoof tissue, as well as by the experience of the veterinarian. It is possible that several thousand shockwaves may be applied.

Studies illustrating the effectiveness of the present invention have been conducted, and over a one year period, seventy-one horses (thirty-seven stallions, thirteen mares and twenty-one geldings) afflicted with podotrochlosis (fifty-four were afflicted bilaterally) were treated. The average age of the horses was 10.6 years.

The first twenty-six subjects were treated over a five month period and included: eight horses affected by a low grade podotrochlosis; fifteen horses affected by a middle grade podotrochlosis; and three horses affected by a high grade podotrochlosis. Of these subjects, nineteen animals were treated bilaterally. Following treatment, at a six month post-treatment check, none of the treated animals showed any visible evidence of lameness.

This invention has been described in terms of specific embodiments, set forth in detail. It should be understood, however, that these embodiments are presented by way of illustration only, and that the invention is not necessarily limited thereto. Modifications and variations within the spirit and scope of the claims that follow will be readily apparent from this disclosure, as those skilled in the art will appreciate.

I claim:

1. A method for treating podotrochlosis in the foot of a horse, the method comprising the steps of:

administering an anesthetic agent to the horse to relax at least the deep digital flexor muscle and the associated tendon in the foot;

extending the length of the deep digital flexor muscle and the associated tendon by flexion or extension;

softening a hoof portion of the foot and shaping the softened hoof to provide a surface for application of a sonar-emitting device and a shockwave-emitting device;

applying the sonar-emitting device to the foot to identify specific areas within the foot affected by podotrochlosis;

applying the shockwave-emitting device to the foot; and directing at least one extracorporeal shockwave from the shockwave-emitting device to an area within the foot identified by the sonar-emitting device as being affected by podotrochlosis.

2. The method according to claim 1, wherein the step of softening the hoof comprises applying an aqueous solution of about 0.9% NaCl to the hoof.

3. The method according to claim 1, further comprising the step of applying a sonar transmission-enhancing agent to the hoof prior to applying the sonar-emitting device to the hoof.

4. The method according to claim 1, wherein the step of extending the length of the deep digital flexor muscle and the associated tendon provides a prolongation of between about 20% and 100%.

5. The method according to claim 4, wherein the prolongation is between about 35% and about 80%.

6. The method according to claim 3, wherein the sonar transmission-enhancing agent is paraffin.

7. The method according to claim 1, further comprising the step of applying a sonar transmission-enhancing agent to the surface for application of the sonar-emitting device and the shockwave-emitting device prior to applying the sonar-emitting device to the hoof.

8. The method according to claim 7, wherein the sonar transmission-enhancing agent is paraffin.

9. The method according to claim 7, wherein the step of extending the length of the deep digital flexor muscle and the associated tendon provides a prolongation of between about 20% and 100%.

10. The method according to claim 9, wherein the prolongation is between about 35% and about 80%.

11. The method according to claim 10, wherein the step of softening the hoof comprises applying an aqueous solution of about 0.9% NaCl to the hoof.

* * * * *